US00PP20133P2

(12) United States Plant Patent
Iwaki

(10) Patent No.: US PP20,133 P2
(45) Date of Patent: Jun. 30, 2009

(54) *ANTIRRHINUM* PLANT NAMED 'SUNKISPINFUFU'

(50) Latin Name: *Antirrhinum majus*
Varietal Denomination: Sunkispinfufu

(75) Inventor: Kazunari Iwaki, Kanagawa (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 12/157,309

(22) Filed: Jun. 9, 2008

(51) Int. Cl.
*A01H 5/00* (2006.01)

(52) U.S. Cl. ..... Plt./322

(58) Field of Classification Search ..... Plt./322
See application file for complete search history.

*Primary Examiner*—Annette H Para
(74) *Attorney, Agent, or Firm*—C. A. Whealy

(57) ABSTRACT

A new and distinct cultivar of *Antirrhinum* plant named 'Sunkispinfufu', characterized by its vigorous, upright and mounded plant habit; freely branching habit and short internodes; dense and bushy plant form; numerous pale pink-colored flowers streaked with red purple; long flowering period; and good garden performance.

1 Drawing Sheet

Botanical designation: *Antirrhinum majus.*
Cultivar denomination: 'Sunkispinfufu'.

BACKGROUND OF THE INVENTION

The present invention relates to a new and distinct cultivar of *Antirrhinum* botanically known as *Antirrhinum majus* and hereinafter referred to by the name 'Sunkispinfufu'.

The new *Antirrhinum* is a product of a planned breeding program conducted by the Inventor in Higashiomi, Shiga, Japan. The objective of the breeding program is to create new compact and freely flowering potted *Antirrhinums* with unique flower coloration.

The new *Antirrhinum* originated from a cross-pollination in Higashiomi, Shiga, Japan in May, 2003 of a proprietary selection of *Antirrhinum majus* identified as code number His97-2, not patented, as the female, or seed, parent with a proprietary selection of *Antirrhinum majus* identified as code number 02Ant33-1, not patented, as the male, or seed, parent. The new *Antirrhinum* was discovered and selected by the Inventor as a flowering plant from within the progeny of the stated cross-pollination in a controlled greenhouse environment in Higashiomi, Shiga, Japan.

Asexual reproduction of the new *Antirrhinum* by cuttings in a controlled greenhouse environment in Higashiomi, Shiga, Japan since April, 2005, has shown that the unique features of this new *Antirrhinum* are stable and reproduced true to type in successive generations.

SUMMARY OF THE INVENTION

The new *Antirrhinum* has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunkispinfufu'. These characteristics in combination distinguish 'Sunkispinfufu' as a new and distinct cultivar of *Antirrhinum:*

1. Vigorous, upright and mounded plant habit.
2. Freely branching habit and short internodes; dense and bushy plant form.
3. Numerous pale pink-colored flowers streaked with red purple.
4. Long flowering period.
5. Good garden performance.

Plants of the new *Antirrhinum* differ from plants of the female parent selection primarily in flower color as plants of the female parent have white-colored flowers.

Plants of the new *Antirrhinum* differ from plants of the male parent selection primarily in flower color as plants of the new *Antirrhinum* have red purple-colored flowers.

Plants of the new *Antirrhinum* can be compared to plants of *Antirrhinum majus* 'Sunkispinfu', disclosed in a U.S. Plant Patent application Ser. No. 12/157,310. Plants of the new *Antirrhinum* differ primarily from plants of 'Sunkispinfu' in flower color as plants of 'Sunkispinfu' have intense pink-colored flowers streaked with red purple.

Plants of the new *Antirrhinum* can also be compared to plants of *Antirrhinum* 'Festa Pink', not patented. In side-by-side comparisons, plants of the new *Antirrhinum* and 'Festa Pink' differed in the following characteristics:

1. Plants of the new *Antirrhinum* were larger and more vigorous than plants of 'Festa Pink'.
2. Plants of the new *Antirrhinum* were more freely branching than plants of 'Festa Pink'.
3. Plants of the new *Antirrhinum* had smaller leaves than plants of 'Festa Pink'.
4. Plants of the new *Antirrhinum* were more freely flowering than plants of 'Festa Pink'.
5. Plants of the new *Antirrhinum* had larger inflorescences and flowers than plants of 'Festa Pink'.
6. Plants of the new *Antirrhinum* and 'Festa Pink' differed in flower color as plants of 'Festa Pink' had red purple-colored flowers.

BRIEF DESCRIPTION OF THE PHOTOGRAPHS

The accompanying colored photographs illustrate the overall appearance of the new *Antirrhinum,* showing the colors as true as it is reasonably possible to obtain in colored reproductions of this type. Colors in the photographs may differ slightly from the color values cited in the detailed botanical description which accurately describe the colors of the new *Antirrhinum*.

The photograph at the top of the sheet comprises a side perspective view of a typical flowering plant of 'Sunkispinfufu' grown in a container.

The photograph at the bottom of the sheet is a close-up view of typical flowers of 'Sunkispinfufu'.

DETAILED BOTANICAL DESCRIPTION

The aforementioned photographs and following observations, measurements and values describe plants grown in Higashiomi, Shiga, Japan, under commercial practice during the autumn in an outdoor nursery with day temperatures averaging 10° C. and night temperatures averaging 5° C. Plants were pinched one time. Plants used for the description had been growing for four months and plants used for the photographs had been growing for nine months. In the following description, color references are made to The Royal Horticultural Society Colour Chart, 2001 Edition, except where general terms of ordinary dictionary significance are used.

Botanical classification: *Antirrhinum majus* 'Sunkispinfufu'.

Parentage:

*Female, or seed, parent.*—Proprietary selection of *Antirrhinum majus* identified as code number His97-2, not patented.

*Male, or pollen, parent.*—Proprietary selection of *Antirrhinum majus* identified as code number 02Ant33-1, not patented.

Propagation:

*Type.*—By vegetative cuttings.

*Time to initiate roots.*—About 10 days at 20° C. to 25° C.

*Time to produce a rooted young plant.*—About 20 days at 20° C. to 25° C.

*Root description.*—Fine, fibrous and fleshy; white in color.

*Rooting habit.*—Freely branching.

Plant description:

*Plant form/habit.*—Vigorous, upright and mounded plant habit; inverted triangle. Freely branching habit with short internodes; dense and bushy plant form.

*Plant height.*—About 20 cm.

*Plant width (spread).*—About 21.2 cm.

*Lateral branches.*—Quantity per plant: About eleven primary branches develop per plant. Length: About 16.1 cm. Diameter: About 2.3 mm. Internode length: About 1.3 cm. Strength: Moderately strong. Texture: Smooth, glabrous. Color: Close to 144A.

Foliage description:

*Arrangement.*—Before flowering, opposite, simple; after flowering, alternate, simple.

*Length.*—About 4 cm.

*Width.*—About 1.1 cm.

*Shape.*—Lanceolate.

*Apex.*—Acute.

*Base.*—Cuneate.

*Margin.*—Entire.

*Texture, upper and lower surfaces.*—Smooth, glabrous.

*Venation pattern.*—Pinnate; reticulate.

*Color.*—Developing leaves, upper surface: Close to 137A. Developing leaves, lower surface: Close to 138A. Fully expanded leaves, upper surface: Close to 137A; venation, close to 138B. Fully expanded leaves, lower surface: Close to 138B; venation, close to 138B.

*Petioles.*—Length: About 9 mm. Diameter: About 0.8 mm. Texture, upper and lower surfaces: Smooth, glabrous. Color, upper and lower surfaces: Close to 138B.

Flower description:

*Flower type/habit.*—Single bi-labiate flowers arranged in terminal and axillary racemes; flowers face outward. Freely flowering habit with about three to five flowers per inflorescence and about 18 inflorescences per plant at one time.

*Fragrance.*—Not detected.

*Natural flowering season.*—Flowering from the early autumn until early summer in Japan. Flowers not persistent.

*Postproduction longevity.*—Flowers last about five days on the plant.

*Flower buds.*—Height: About 3 cm. Diameter: About 1.3 cm. Shape: Cylindrical. Color: Close to 65D, streaked with close to 71B.

*Inflorescence height.*—About 7.1 cm.

*Inflorescence diameter.*—About 7.3 cm.

*Flower diameter.*—About 3.3 cm to 3.4 cm.

*Flower depth (height).*—About 3.8 cm.

*Throat diameter.*—About 8 mm.

*Tube length.*—About 1.9 cm.

*Petals.*—Quantity per flower: Upper lip, two-lobed; lower lip, three-lobed; petals fused at the base. Length, upper lip: About 2.1 cm. Width, upper lip: About 3.6 cm. Length, lower lip: About 1.7 cm. Width, lower lip: About 3.4 cm. Apex, upper and lower lips: Rounded, obtuse. Margin, upper and lower lips: Entire. Texture, upper and lower lips, upper and lower surfaces: Smooth, glabrous. Color: When opening and fully opened, upper and lower petals, upper surface: Close to 69B, streaked with close to N78B. When opening and fully opened, upper and lower petals, lower surface: Close to 69B, streaked with close to N78B. Throat: Close to 69D. Tube: Close to 69D, streaked with close to N78B.

*Sepals.*—Quantity per flower: Typically five in a single whorl. Length: About 8 mm. Width: About 4.5 mm. Shape: Ovate. Apex: Acute. Margin: Entire. Texture, upper and lower surfaces: Smooth, glabrous. Color, upper surface: Close to 146B tinted with close to N199A. Color, upper surface: Close to 146B.

*Pedicels.*—Length: About 7 mm. Diameter: About 1.4 mm. Strength: Strong. Texture: Pubescent. Color: Close to 144A.

*Reproductive organs.*—Stamens: Quantity per flower: Typically four. Stamen length: About 2.2 cm. Anther size: About 3 mm by 2.6 mm. Anther shape: Oval, bi-lobed. Anther color: Close to 13B. Pollen amount: Moderate. Pollen color: Close to 13B. Pistils: Quantity per flower: One. Pistil length: About 1.7 cm. Stigma shape: Club-shaped. Stigma color: Close to N144A. Style color: Close to 185D. Ovary color: Close to 144D.

*Seeds/fruits.*—Seed and fruit development have not been observed.

Disease/pest resistance: Plants of the new *Antirrhinum* have not been noted to be resistant to pathogens and pests common to *Antirrhinum*.

Garden performance: Plants of the new *Antirrhinum* have been observed to have excellent garden performance and tolerate rain, wind and temperatures ranging from about −10° C. to about 30° C.

It is claimed:

1. A new and distinct *Antirrhinum* plant named 'Sunkispinfufu' as illustrated and described.

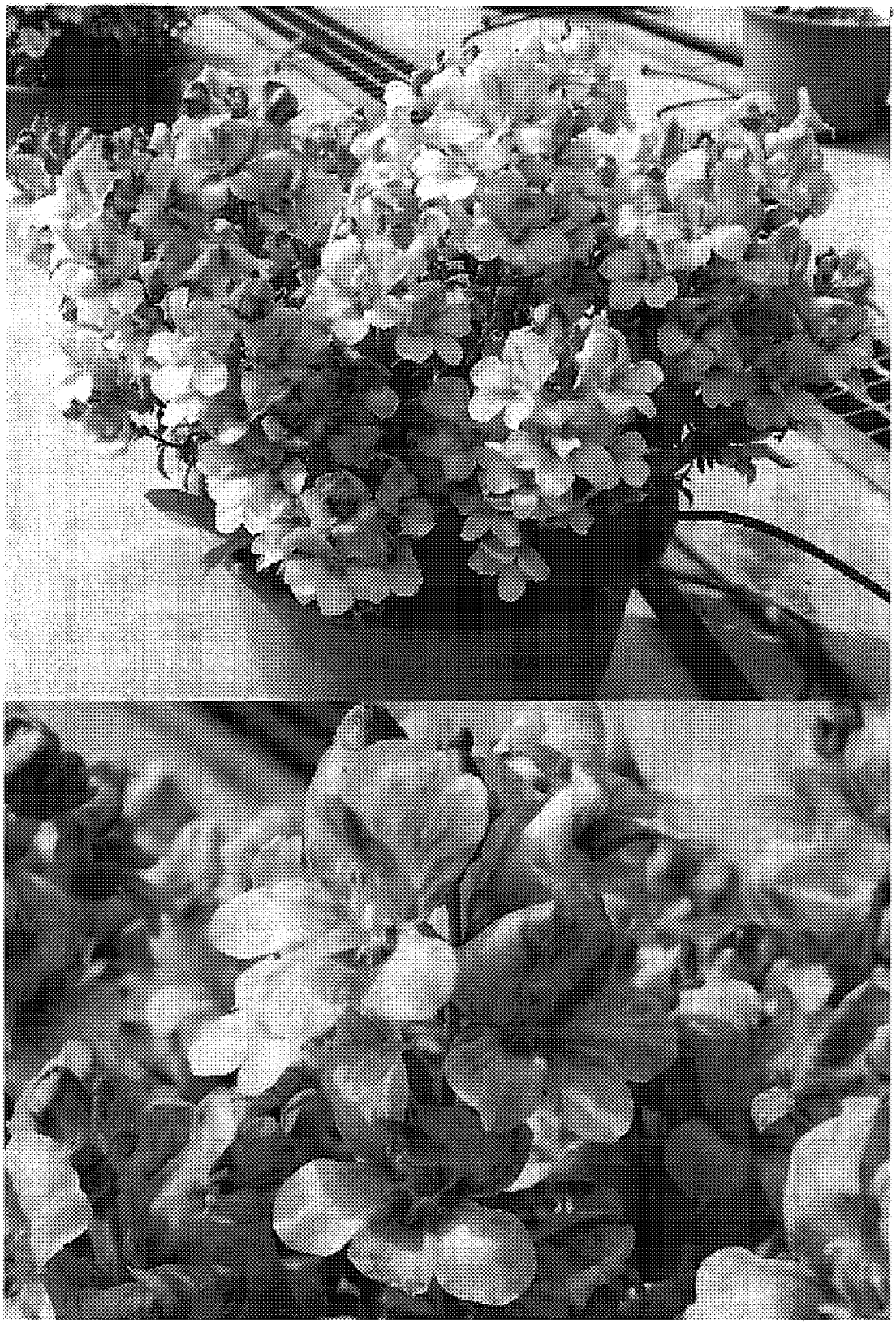

* * * * *